(12) United States Patent
Herbert

(10) Patent No.: US 6,905,584 B2
(45) Date of Patent: Jun. 14, 2005

(54) ELECTROPHORESIS SYSTEM AND METHOD THEREFOR

(75) Inventor: Ben Herbert, North Epping (AU)

(73) Assignee: Proteome Systems Limited (AU)

(*) Notice: Subject to any disclaimer, the term of this patent is extended or adjusted under 35 U.S.C. 154(b) by 238 days.

(21) Appl. No.: 09/966,352

(22) Filed: Sep. 28, 2001

(65) Prior Publication Data

US 2002/0100690 A1 Aug. 1, 2002

(30) Foreign Application Priority Data

Sep. 29, 2000 (AU) .............................................. PR0515

(51) Int. Cl.⁷ .......................................... G01N 27/447
(52) U.S. Cl. ...................... 204/456; 204/459; 204/467
(58) Field of Search ................................ 204/456, 457, 204/459, 467, 606, 608, 610, 618

(56) References Cited

U.S. PATENT DOCUMENTS

| | | | | |
|---|---|---|---|---|
| 3,715,295 A | * | 2/1973 | Tocci ........................... | 204/456 |
| 3,773,646 A | * | 11/1973 | Mandle et al. ............... | 204/620 |
| 3,803,020 A | | 4/1974 | Stephan | |
| 4,101,401 A | | 7/1978 | Hoefer | |
| 4,385,974 A | * | 5/1983 | Shevitz ........................ | 204/464 |
| 4,666,581 A | * | 5/1987 | Itoh et al. .................... | 204/616 |
| 4,874,490 A | | 10/1989 | Hochstrasser | |
| 5,773,645 A | * | 6/1998 | Hochstrasser ............... | 204/456 |

FOREIGN PATENT DOCUMENTS

| | | |
|---|---|---|
| DE | 3735872 A | 8/1989 |
| EP | 0171680 A | 2/1986 |
| EP | 0287513 A | 10/1988 |
| WO | WO 92/00795 A | 1/1992 |
| WO | WO 98/25136 A | 6/1998 |
| WO | WO 00/02039 | 1/2000 |

* cited by examiner

Primary Examiner—Kaj K. Olsen
(74) Attorney, Agent, or Firm—Sonnenschein Nath & Rosenthal LLP

(57) ABSTRACT

A method for separating a sample into components by two-dimensional electrophoresis uses an IPG strip, and a gel slab which are spaced apart and carried on a single generally planar support means. The planar support means is first oriented in a generally vertical plane and the first electrophoretic separation medium is oriented in a horizontal plane spaced above or below the second electrophoretic separation medium by a gap. A first dimension separation of a sample mixture in the strip is then carried out while the strip and slab are separated by a non-electrically conducting liquid which is substantially immiscible with water and is non-extractive of water preferably paraffin oil. After the first separation has been carried the support means is tilted so that the first strip is at an angle to the horizontal and the paraffin is flushed out from the gap between the strip and the slab. Next agarose gel containing buffer is flowed into the gap to allow transfer of sample molecules from the strip to the slab under the influence of an electric field.

7 Claims, 10 Drawing Sheets

ELECTROPHORESIS SYSTEM AND METHOD THEREFOR

This application claims priority of Australian Provisional Patent Application Serial No. PR 0515, filed Sep. 29, 2000.

FIELD OF THE INVENTION

The present invention relates to a method for performing two-dimensional electrophoresis whereby both first and second dimension gels are contained within a single cassette.

BACKGROUND OF THE INVENTION

For the last 25 years, 2-D PAGE (two-dimensional polyacrylamide gel electrophoresis) has been the technique of choice for analysing the protein composition of a given cell type and for monitoring changes in gene activity through the quantitative and qualitative analysis of the thousands of proteins that orchestrate various cellular functions. Despite its extraordinary resolving power, 2-D PAGE has never been adopted for high throughput screening studies. This is because the first and second dimension gels are run separately, thus requiring two different running devices and making automation difficult. In addition, a high level of operator skill and knowledge is required to successfully complete a 2-D gel.

To achieve truly high throughput and reproducibility of 2-D gels it will be necessary remove as much of the operator intervention as possible. This could be accomplished by combining the first and second dimension gels in a single cassette and thus removing the need for the operator to interface the gels manually. This manual interfacing step is slow and cumbersome and a source of inter-operator differences thus leading to a lack of reproducibility. Another advantage of combining the two gels in a single cassette is the reduction of the running hardware to a single apparatus, thus increasing the possibilities of automation. Placing the gels together in a single cassette requires the ability to place the gels within a few millimetres of each other while maintaining the separation between the gels until the transfer of protein from the first to the second dimension is required. There are serious technical difficulties associated with combining the first and second dimension gels in a single cassette. Firstly, the solutions present, and thus the ionic conditions, in the two gels are quite dissimilar. The first dimension, isoelectric focusing, gel has very low ionic strength and is not compatible with high levels of salts or buffers. Isoelectric focusing is performed at high voltage, up to 10,000 volts, and very low current, typically below 1 mA per gel. Conversely the second dimension gel has a high concentration of buffer salts, usually in the 100 to 500 mM range, and the electrophoresis is performed at high currents in the range of 5 to 100 mA per gel. Thus, when placing these two gels in close proximity care must be taken to ensure that there is no contamination of the first dimension gel with buffer from the second dimension gel, which would result in very high current and subsequent burning of the first dimension gel.

The second problem that one faces is the loading of the sample onto the first dimension gel without allowing any of the sample to prematurely transfer to the second dimension gel. The best way of performing isoelectric focusing is to use immobilised pH gradients (IPG), which are typically supplied as dry strips and rehydrated with the sample solution, thus distributing the sample over the entire gel, which allows high protein loads. When the two gels are combined in a single cassette it is difficult to wet the entire surface of the IPG with sample without allowing some of the sample to transfer to the second dimension gel.

Attempts have been made to provide combined strip gels and slab gels for carrying out 2-dimensional electrophoresis. U.S. Pat. No. 4,874,490 discloses such an apparatus. However the proposed method is unwieldy and impractical and no examples of the method being carried out and actually working are given. With the recent upsurge in interest in the field of proteomics it becomes necessary to carry out many more separations than have previously been done. Separations, particularly two-dimensional separations are labour intensive and the only practical way of increasing the productivity of workers in the field is to provide methods and systems which are susceptible to automation. The method shown in U.S. Pat. No. 4,874,490, if it works at all, would be difficult, if not impossible, to mechanise.

U.S. Pat. No. 5,773,645 discloses a further apparatus for carrying out a two-dimensional separation on a common support. Again this specification does not disclose any examples or results from using the apparatus. Further the system disclosed would again be difficult and expensive to automate.

One object of the present invention is to provide a new method which overcomes the technical difficulties associated with combining and running the first and second dimension gels in a single cassette in an manner which may allow the method and system to be automated.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

SUMMARY OF THE INVENTION

In a first broad aspect, it is the underlying idea of the present invention to propose a novel method for allowing a first dimension isoelectric focusing gel and a second dimension electrophoresis gel to be combined, stored, shipped and run in a single cassette which is susceptible to automation.

In a second aspect the invention provides methods for rehydrating the first dimension gel with a solution of the sample proteins or polypeptides. Said rehydration occurs in the cassette without transfer of the sample solution to the second dimension gel.

In a third aspect the invention provides a method for placing a current insulating barrier between the first and second dimension gels while the isoelectric focusing is performed. The barrier prevents dehydration of both gels in the cassette and additionally prevents any premature transfer of sample from the first dimension gel to the second dimension gel or transfer of buffer salts from the second dimension gel to the first dimension gel.

Another aspect of the invention is a method for removing the current insulating barrier and providing a buffer impregnated, electrically conductive, bridging material, preferably a gel, to connect the first dimension gel with the second dimension gel. The bridging material allows proteins to transfer from the first dimension gel to the second dimension gel.

A further aspect of the invention is a means for providing electrical connections to the ends of the first dimension gel to allow the electrophoresis to proceed.

In a particular aspect there is provided a method for separating a sample into components by two-dimensional electrophoresis, said method comprising:

providing a first electrophoretic separation medium comprising an elongate strip, typically an IPG strip, and a second electrophoretic separation medium, typically in the form of a slab, said media being spaced apart and carried on a single generally planar support means;

with the planar support means oriented in a generally vertical plane and the first electrophoretic separation medium oriented in a horizontal plane spaced above or below the second electrophoretic separation medium by a gap, carrying out a first dimension separation of a sample mixture in the first electrophoretic separation medium, while the first and second media are separated by a non-electrically conducting liquid which is of low viscosity, low volatility and substantially nonflammable, is substantially immiscible with water and is non-extractive of water;

after the first separation has been carried out tilting the support means so that the first electrophoretic separation medium is at an angle to the horizontal and flushing the liquid out from the gap between the first electrophoretic separation medium and the second electrophoretic separation medium; and flowing a liquid buffer containing bridging material, typically agarose gel containing buffer, into the gap to allow transfer of sample molecules from the first electrophoretic separation medium to the second electrophoretic separation medium under the influence of an electric field.

The term non-extractive of water as used herein covers liquids which are completely immiscible with water and thus do not absorb or adsorb any water. There are a number of solvents which are commonly described as being immiscible with water but which in fact can absorb quantities of water before becoming saturated and forming two layers. Such solvents are generally unsuited for use in the present invention since they may withdraw water from, and thus dehydrate, the gel or IPG strip if they are not already water saturated, and if saturated do not electrically insulate sufficiently well over the relatively long period the first dimension separation is run on the IPG strip which can take from 12 to 48 hours.

It is preferred that the first electrophoretic separation medium is at least partly enclosed by a removable cover which allows the medium to be rehydrated, typically using a liquid containing the sample to be separated while the support means is in the vertical orientation.

The removable cover is most preferably made from a metallic foil or the like. IPG strips have a shelf life which depends on the conditions under which they are kept. If kept totally dry, IPG strips can last for many years. However air can cause oxidation of the strips, and water vapor which is present in atmospheric air also increases the rate of degradation of the strips so a gastight seal is preferred. The shelf life of the 2 D gel slab is typically one year hence it is desirable that the seal on for the IPG maintains the IPG strip in good condition for at least that length of time. Plastic films, in contrast do not provide a good seal as they are not as gastight as metal foil and are unlikely to keep the IPG for the requisite period of one year.

The fact that the entire two dimensional electrophoresis separation may be carried out with the support means in the same vertical orientation facilitates the mechanisation of the system as compared with the prior art where the support means may be horizontally or both horizontally and vertically oriented.

The non-conducting liquid is most preferably paraffin oil which is water immiscible, is very hydrophobic and non-extractive of water and has a relatively low viscosity. The low viscosity is advantageous as it allows the paraffin oil to fill the relatively narrow (typically 1 mm to 4 mm) and convoluted gaps between the IPG strip and the gel slab. Depending on the gap size, oils with viscosities of up to 30 $mm^2/s$ are preferred, typically 10–25 $mm^2/s$ are used. More viscous materials would require a wider gap. This would be disadvantageous as the agarose which is used to bridge the gap has a larger pore size than both the IPG strip and the 2d gel slab. Thus diffusion tends to occur in the agarose gel and the narrower the gap the better as the run time is shorter and less diffusion takes place.

BRIEF DESCRIPTION OF THE DRAWINGS

Specific embodiments of the invention will now be described by way of example only and with reference to the accompanying drawings in which.

DESCRIPTION OF THE PREFERRED EMBODIMENTS OF THE INVENTION AND EXAMPLES

Figure 1:
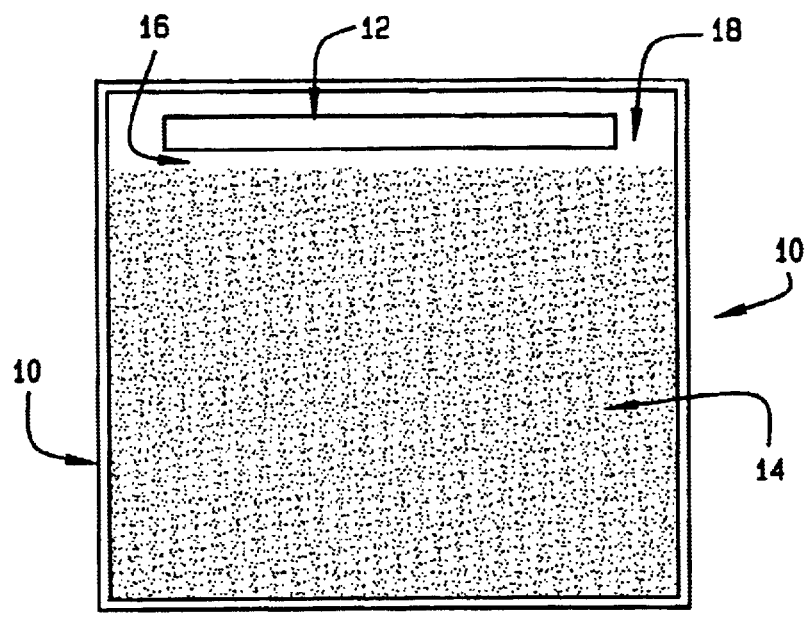
FIG. 1 is a schematic side view of a combined 2-D gel showing the IPG and second dimension gel positioned together in a single cassette.
Figure 2:
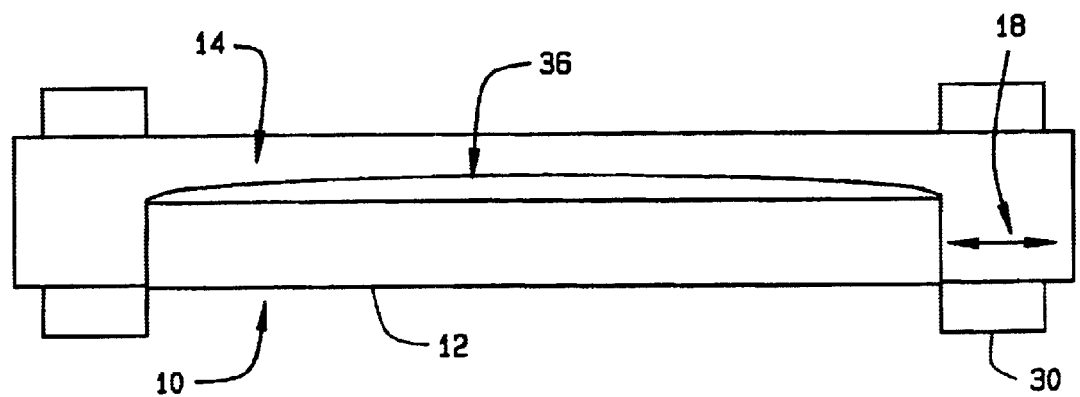
FIG. 2 is a schematic top view of a combined 2-D gel showing the IPG and second dimension gel positioned together in a single cassette.

Referring to the drawings FIGS. 1 and 2 show the side and top views respectively of a combined 2-D gel cassette 10 with a first dimension gel typically a dry immobilised pH gradient (IPG) type of gel 12, and a second dimension gel 14. The cassette may be made of glass or plastic or any other suitable material.

The IPG 12 is spaced by a gap 16 of about 2 mm away from the top surface of the second dimension gel and is oriented substantially parallel to the top surface of the second dimension gel. A gap 18 of approximately 5 mm is maintained between the ends of the IPG 12 and the sides of the cassette 10 to allow the insertion of electrode bridge material for the second separation. Although the devices shown in the figures have a single IPG 12 placed parallel to the top of the second dimension gel and spaced at approximately 2 mm from the second dimension gel, it will be clear to those skilled in the art that a combined 2-D gel of this design could be made to contain one or more IPGs in a linear array, spaced at more or less than 2 mm from the top of the second dimension gel.

Figure 3:
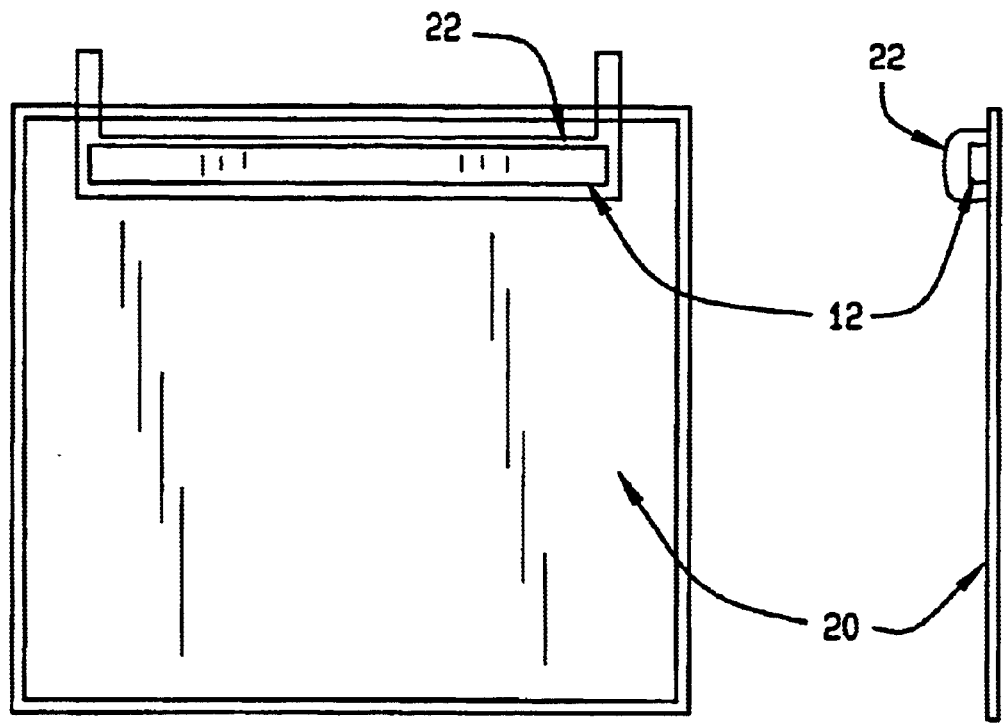
FIG. 3 shows two schematic side views of a single cassette plate prior to the assembly and casting of the second dimension gel. The IPG is attached to the cassette plate and is covered with a thin layer of plastic.
Figure 4:
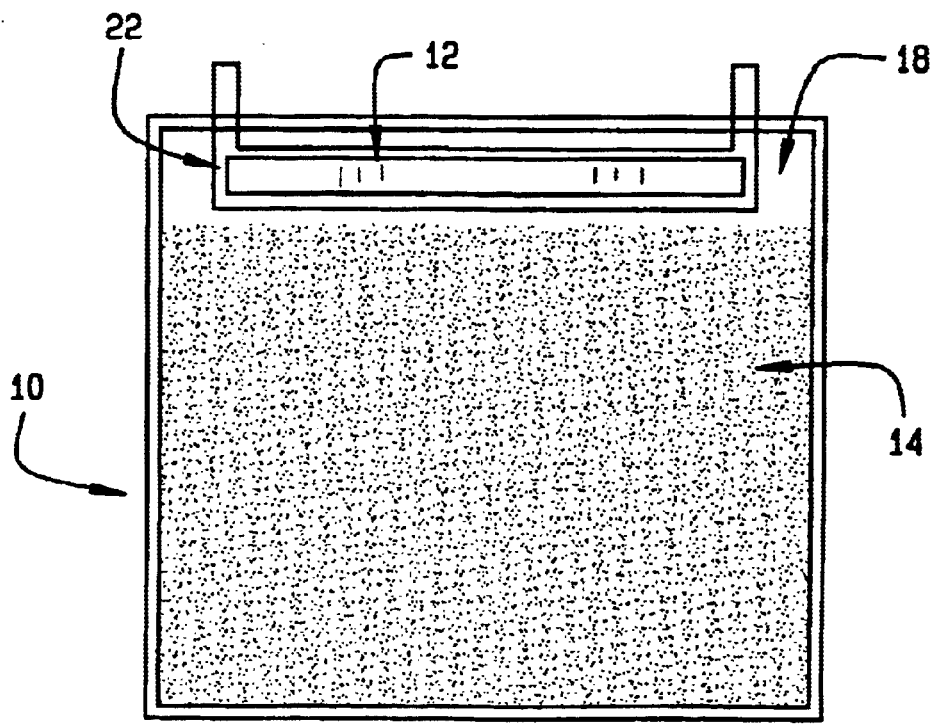
FIG. 4 shows a fully assembled cassette as in FIG. 1 where the IPG is covered with a plastic cover sheet as in FIG. 3
Figure 5:
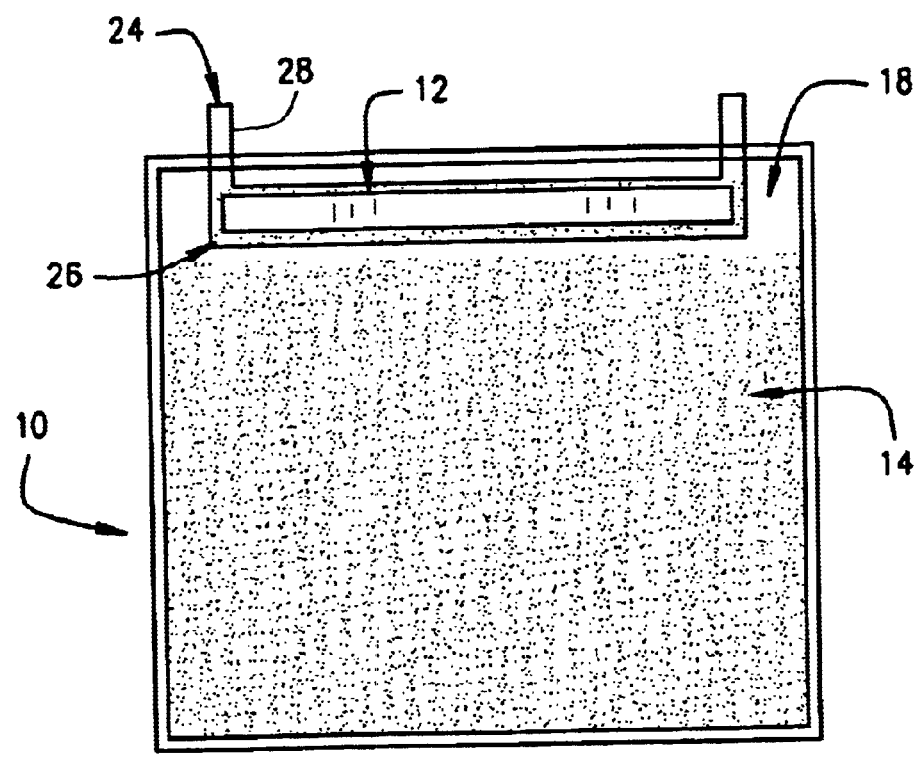
FIG. 5 shows a cassette as depicted in FIG. 4 where rehydration liquid has been introduced into the gap, containing the IPG, between the cassette wall and the plastic cover sheet.

In a preferred embodiment the IPG is fixed to a single plate 20 of the cassette as shown in FIG. 3. The dry IPG is covered with a thin metal foil cover sheet 22, which is also fixed to the cassette plate to provide a liquid impermeable barrier, as shown in FIG. 3. IPG strips typically have a shelf life which depends on the conditions under which they are kept. If kept totally dry and refrigerated or frozen, IPG strips can last for many years. However air can cause oxidation of the strips, and water vapor which is present in atmospheric air also increases the rate of degradation of the strips so a gastight seal such as can be provided by a metal foil is preferred. The shelf life of the 2D gel slab is typically one year hence it is desirable that the seal on for the IPG maintains the IPG strip in good condition for at least that length of time. The sheet may be made of materials other than metal foil however they should be gas impermeable. The front plate of the cassette 10 is subsequently attached and the second dimension gel 14 is cast within the cassette, thus producing the finished cassette.

To load the sample, a small hole is made in one of the ears 158 in the cover sheet 156, and introducing the liquid sample into the space surrounding the IPG 12 formed by the cover. It is important to introduce only enough liquid to rehydrate the IPG 12, as any liquid which is not absorbed will contain protein and thus diminish the load. The dry IPG 12 is allowed to rehydrate until all the liquid has been absorbed. After the rehydration process the cover 156 is removed by peeling it away from the cassette using one or both of the ears 158 as a handle.

Alternatively but less advantageously it is possible to load the sample in a cassette as in FIG. 1 which does not have an IPG cover. In this embodiment the cassette, as shown in FIG. 1, is placed horizontally as shown in FIG. 2, with the IPG gel facing up or down and rehydration liquid 36 is carefully placed onto the surface of the IPG using a syringe. Capillary action holds the rehydration liquid 36 onto the IPG surface and air acts as a barrier in the gap between the IPG and the second dimension gel, preventing the rehydration liquid 36 from contacting the second dimension gel. Although the embodiment of the cassette shown in FIG. 1 shows uses air as the barrier between the gels during the rehydration process it will be clear to those skilled in the art that a combined 2-D gel of this design could use gases other than air, or liquids or solids as the barrier during the rehydration.

Figure 6:
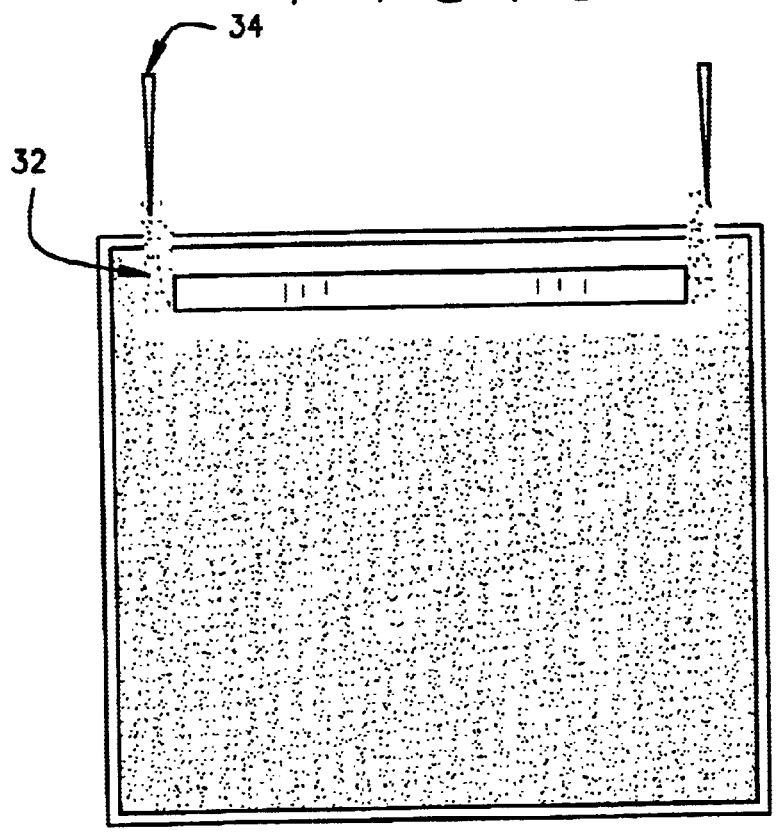
FIG. 6 is a schematic side view of a combined 2-D gel showing the positioning of the electrode bridge material and the electrodes at each end of the IPG gel
Figure 7:
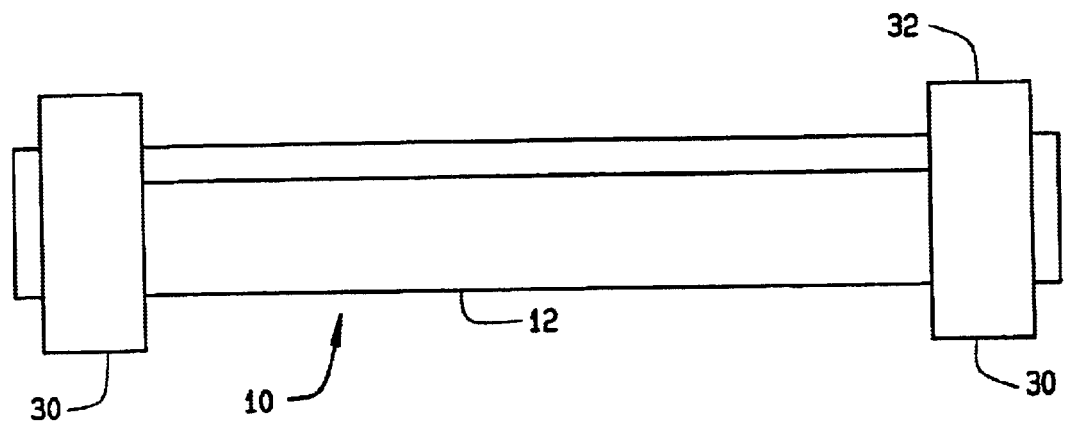
FIG. 7 is a schematic top view of a combined 2-D gel showing the positioning of the electrode bridge material at each end of the IPG gel

After the IPG gel has been rehydrated an electrode bridge must be placed in contact with each end of the IPG, as shown in FIGS. 6 and 7. As shown in FIG. 7 the electrode bridge material 32 is held in place inside widened regions 30 of the cassette at each end. The electrode bridge material is commonly thick filter paper, cut to size and wetted with purified water. The advantage of having widened regions 30 is that larger thicker pieces of filter paper can be used as the bridge material. This is advantageous since during the application of an electric field to the gel the bridge material acts to soak up stray ionic material that is not wanted in the IPG. However, the electrode material could be made of any solid, inert, non-ionic, water absorptive material. In addition, in some cases it is desirable to soak the electrode material in buffers or sample solubilising solutions such as those used for IEF. For example, IEF solubilising solution may be used when highly solubilising conditions are required in the electrode bridge material to facilitate the removal of proteins which are not isoelectric within the IPG pH range. The electrode material acts as a reservoir between the gel and the electrode, where ionic contaminants and non-isoelectric proteins from the sample can collect without disrupting the separation. The advantage of having widened regions 30 is that larger thicker pieces of filter paper can be used as the bridge material which can soak up more stray ionic material. As shown in FIG. 6 the electrodes 34 are usually pin shaped to allow penetration, and good contact, in the electrode bridge material.

In use, after the insertion of the electrode bridge material, the gap between the IPG and the second dimension gel is filled with a barrier material to prevent dehydration of the IPG during the IEF step and to prevent conduction across the gap. In addition, the barrier prevents any transfer of liquid between the first and second dimension gels during the IEF. The barrier material must be immiscible with water and non-extractive of water ie must not absorb or adsorb any water. There are a number of solvents which are commonly described as being immiscible with water but which in fact can absorb quantities of water before becoming saturated and forming two layers. Such solvents are generally unsuited for use in the present invention since they may withdraw water from the gel or IPG strip if they are not already water saturated and if saturated do not insulate sufficiently well over the relatively long period the first dimension separation is run on the IPG strip which can take from 12 to 48 hours.

Figure 8:
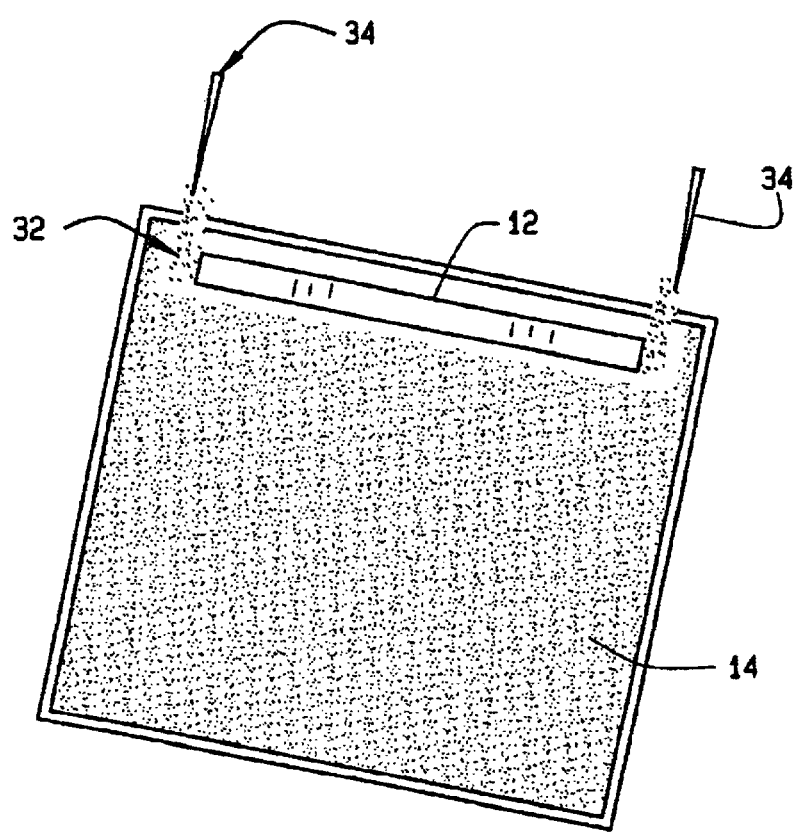
FIG. 8 is a schematic side view of a combined 2-D gel as in FIG. 3, where the cassette has been tilted to facilitate loading of the paraffin oil barrier material

In a preferred embodiment the barrier material is light paraffin oil, such as the "Shell Ondina Oil 15" supplied by the Shell Company of Australian Limited of 1 Spring Street, Melbourne, VIC, 3000, Australia which is purified white medicinal paraffin oil severely refined to remove any substance with any degree of chemical activity and is consequently a very bland, chemically inert, water white product. The product is available in ISO viscosity grades 32 and 68, however, ISO 15 is the preferred viscosity grade having a typical viscosity at 40° C. of 15.6 mm$^2$/s. However, it will be clear to those skilled in the art that paraffin oil with higher or lower density, or other oils may be suitable barrier materials provide that they meet the characteristics set out above. The barrier material is most preferably liquid at room temperature. The paraffin oil is inserted using a pipette with the cassette in a vertical position as shown in FIG. 8. The electrodes are placed into the electrode bridge material and the IEF is performed with the cassette in a vertical position.

To facilitate the transfer of protein from the IPG to the second dimension gel after the IEF the IPG requires equilibration with a suitable buffer. In a typical 2-D gel the equilibration buffer contains reducing agents such as dithiothreitol or tributyl phosphine and the surfactant Sodium Dodecyl Sulfate (SDS) which binds to the proteins and confers an overriding negative charge. The negative charge allows separation of the proteins according to molecular weight in the second dimension. In a preferred embodiment of this invention the IPG equilibration and SDS binding is done by displacing the paraffin oil barrier with a solution of molten 0.5% agarose containing SDS, and the appropriate buffer. In the preferred embodiment the proteins are reduced and alkylated prior to the first dimension separation. However, if the proteins have been separated in their reduced forms in the first dimension a reducing agent such as dithithreitol or tributyl phosphine is added to the agarose. The molten agarose (typically 1–5 mL) solution is flushed through the gap between the first and second dimension gels, thus thoroughly removing the paraffin oil. Finally molten agarose containing SDS, glycerol and buffer is allowed to set in the gap between the first and second dimension gels, thus bridging the gap and allowing for protein transfer. To facilitate the addition of the hot agarose it is essential to have the cassette in a tilted vertical position as shown in FIG. 8. When the air bubbles have been flushed out of the gap the cassette is returned to a normal vertical position as in FIG. 6 and allowed to stand at room temperature for 20 minutes to allow the agarose to set and the TBP and SDS to diffuse into the IPG. The standing time may be varied from zero to more than 20 minutes depending on the sample and the protein load. This system is particularly preferred as it is simple and lends itself to automation.

In a second less preferred, embodiment of the current invention a conventional equilibration solution, containing urea, SDS, reducing agents, buffer and glycerol can be flushed through the gap, displacing the paraffin barrier. This equilibration solution is allowed to remain in the cassette for between 5 minutes and 30 minutes and is usually changed up to 10 times, however it will be clear to those skilled in the art that the equilibration time and the number of changes may be varied without departing from the spirit of the invention or damaging the resulting gel.

Figure 9:
FIG. 9 is a silver stained two-dimensional gel run using the cassette arrangement described in FIGS. 1 to 4.

The running of the second dimension gel and the subsequent staining are performed according to normal procedures. FIG. 9 shows a silver stained 2-D gel of Rat liver run in a cassette as shown in FIG. 1. It is clear that the rehydration and IEF steps have worked well and the barrier materials used have prevented any premature transfer of the sample to the second dimension.

Figure 10:
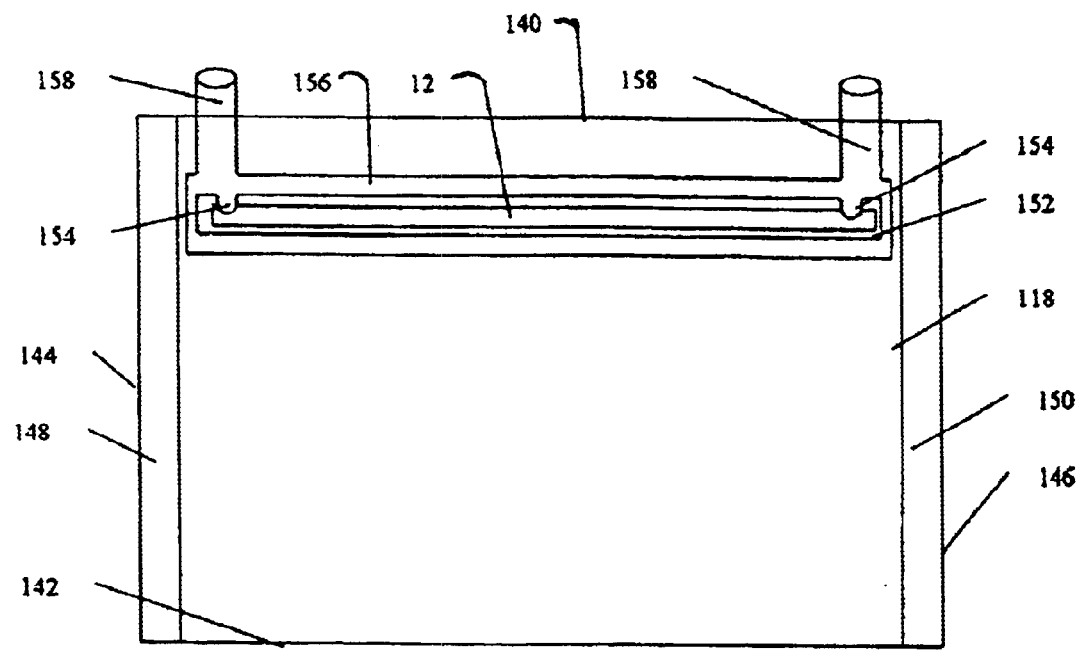
FIG. 10 is a front elevation view of the back plate of a cassette constructed according to the principles of this invention.
Figure 11:
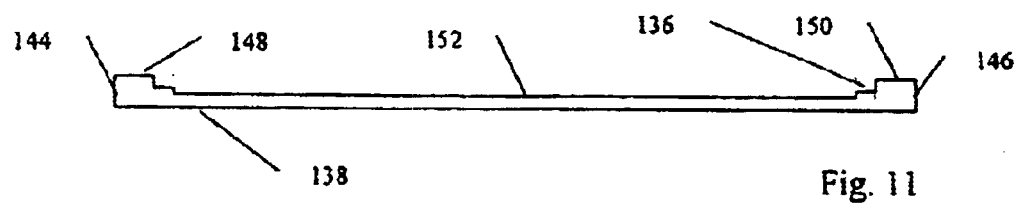
FIG. 11 is a transverse cross-sectional view of the back plate, taken along the plane of line 11—11 in FIG. 10.
Figure 12:
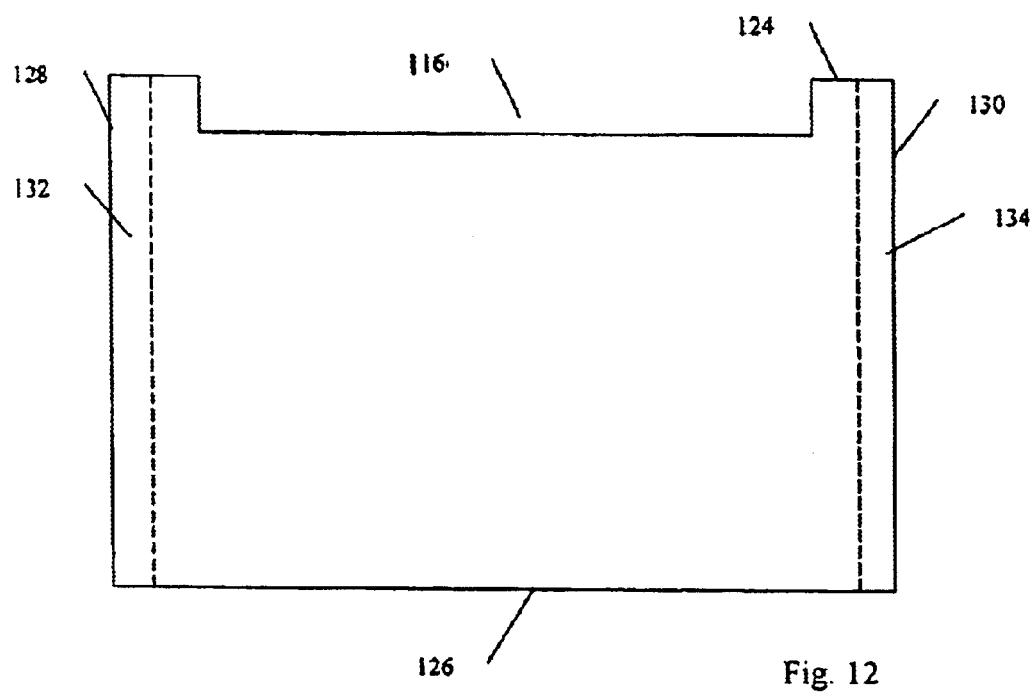
FIG. 12 is a front elevation view of the front plate of the cassette.
Figure 13:
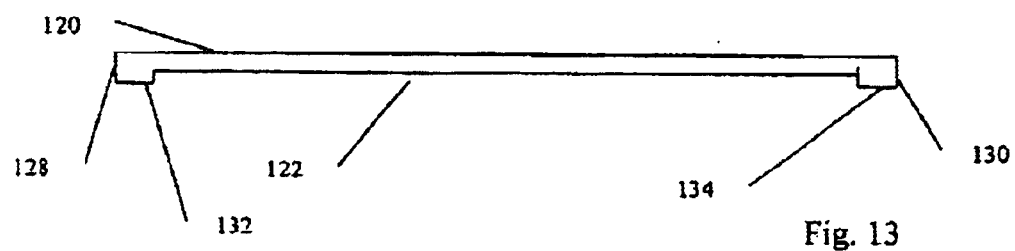
FIG. 13 is a transverse cross-sectional view of the front plate, taken along the plane of line 13—13 in FIG. 12.

In one preferred embodiment, the cassette 10 comprises a front panel 116 and a back panel 118. As shown in FIGS. 12 and 13 the front panel 116 has a front face 120, a back face 122, and top, bottom, left and right side edges 124, 126, 128, and 130. Spacing strips 132 and 134 are provided on the back face 122 of the front panel 116, adjacent the left and right sides 128 and 130. As shown in FIGS. 10 and 11, the back panel 118 has a front face 136, a back face 138, and top, bottom, left and right side edges 140, 142, 144, and 146. Spacing strips 148 and 150 are provided on the front face 132 of the back panel 118, adjacent the left and right side edges 142 and 144. The front panels can be made of plastic, glass, or other suitable material. Plastic is preferred because it can be transparent, and is relatively inexpensive and easy to form.

Figure 15A:
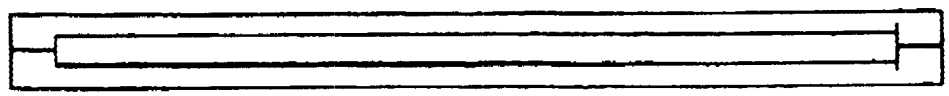
Figure 15B:
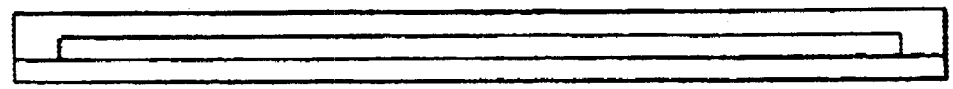
Figure 15C:
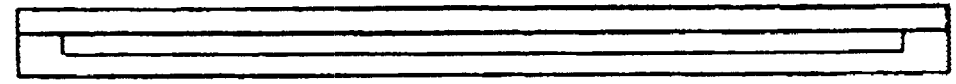
Figure 15D:
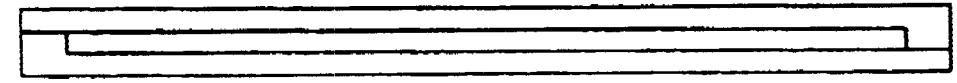
Figure 15E:
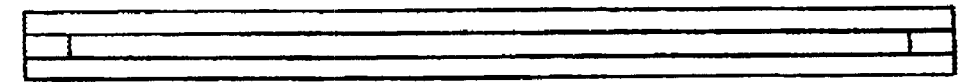

The front and back panels 116 and 118 are joined together with the front face 136 of the back panel 118 facing the back face 122 of the front panel 116, and the spacer strips 132 and 134 aligned with the spacer strips 148 and 150. The front and back panels 116 and 118 can be joined with an adhesive, ultrasonic welding, or any other suitable means. The spacer strips 132 and 134 on the front panel 116 and the spacer strips 148 and 150 on the rear panel 118 can be configured with intermitting and/or interlocking portions to help align the panels, and to help hold the panels together. In alternative constructions, the spacers could be provided just on the front panel 116 (see FIG. 15B), or just on the back panel 118 (see FIG. 15C), or the spacer on one side of the cassette could be provided on the front panel and the spacer on the other side of the cassette could be provided on the back panel (see FIG. 15D). Further, separate spacers could be provided on the back panel (see FIG. 15E). In still another alternative construction, a spacer can be provided between the front and rear panels along their respective bottom edges. This spacer could be formed by spacer strips on the front and back panels, or on just the front or back panel, or as a separate piece. However, it is usually preferable that the cassette 10 be open at the bottom for ease of forming the second dimension gel 14.

The front face 136 of the back panel 118 preferably has an indentation or recess 152 for receiving and holding the IPG 12. The IPG 12 can be secured in the indentation or recess 152 with an adhesive, or clips or anchors can be provided to sercure the IPG. In this preferred embodiment, resilient clips 154 formed integrally with the rear panel, are provided to secure the IPG in the recess 152. A removable cover 156 is provided over the IPG 12. The cover 156 preferably seals with, but can readily be removed from, the back panel 118. The cover 156 protects the IPG 12, and provides a convenient way to rehydrate the IPG. The cover 156 is preferably made from a flexible sheet material, and has at least one and preferably two "ears" 158 extending upwardly beyond the top of the cassette 10, so that the ears can be conveniently accessed to open the cover to rehydrate the IPG 12, and thereafter grasp the cover to remove it from the back panel 118. These ears 158 are preferably in the form of closed-end tubes. The cover 156 is preferably made from a metal foil so that it is strong and flexible yet provides a liquid and gas tight seal. The electrical conductivity of the metal foil also helps resist local corrosion that could degrade the cover and/or the IPG 12. The metal foil could be combined with a conductive plastic layer, such as a film or paint, which improves corrosion resistance and strength of the cover so that it resists fragmentation during removal. The cover 156 can be secured with an adhesive or by ultrasonic welding. An adhesive that softens with moisture has the advantage of weaking as the IPG 12 is rehydrating to facilitate removal of the cover 156.

Figure 14:
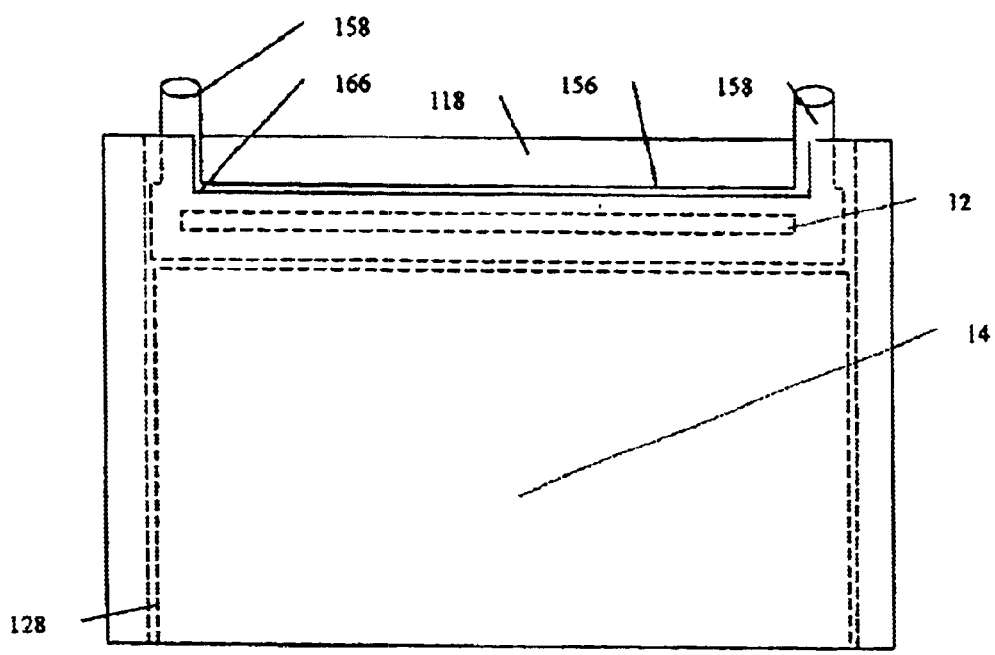
FIG. 14 is a front elevation view of the assembled cassette.
Figure 14A:
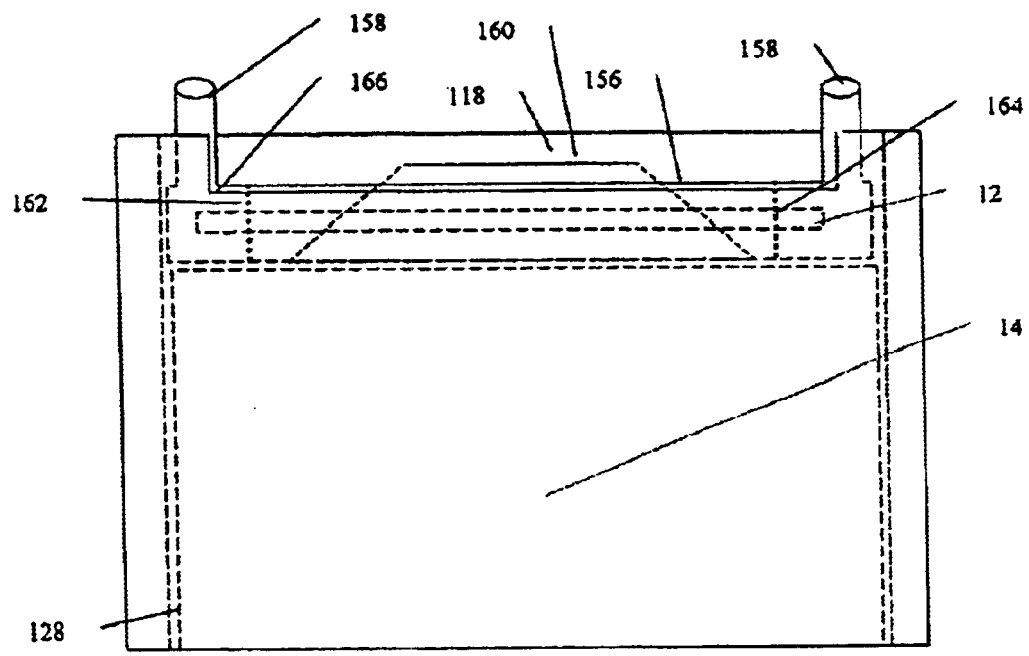
FIG. 14A is a front elevation view of an alternate construction of the assembled cassette and FIGS. 15A–15E are transverse cross sectional views of alternate constructions of the cassette.

In an alternative construction, shown in FIG. 14A, the cover 156 is constructed with tab 160 and lines of weakness 162 and 164 so that the when the tab is pulled, only the center portion of the cover is removed, leaving the end portions, which because of their electrical conductivity can be used as electrodes for the first separation. Other alternative constructions of the cover include a rigid cover, rather than a flexible cover.

Grooves or channels can be formed in the front face 136 of the back panel 118, to facilitate the insertion of paper electrodes to contact the IPG 12.

The front panel 116 has a cut-out 166, so that when cassettes 10 are joined face to face, a connected reservoir is formed between them for holding the insulating material during the first stage.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method for separating a sample into components by two-dimensional electrophoresis, said method comprising:
   a. providing a first electrophoretic separation medium comprising an elongate strip, and a second electrophoretic separation medium, said media being spaced apart and carried on a single support means;
   b. with the support means oriented in a generally vertical plane and the first electrophoretic separation medium oriented in a horizontal plane spaced above or below the second electrophoretic separation medium by a gap, carrying out a first dimension separation of a sample mixture in the first electrophoretic separation medium, while the first and second media are separated by a non-electrically conducting liquid which is substantially immiscible with, and non-extractive of, water;
   c. after the first dimension separation of step b has been carried out, tilting the support means so that the first electrophoretic separation medium is at an angle to the horizontal and flushing the liquid out from the gap between the first electrophoretic separation medium and the second electrophoretic separation medium; and
   d. flowing a liquid buffer containing bridging material into the gap;
   e. applying an electric field to transfer sample molecules from the first electrophoretic separation medium to the second electrophoretic separation medium.

2. A method as claimed in claim 1 wherein the first electrophoretic separation medium is at least partly enclosed by a removable metal foil cover which allows the medium to be rehydrated, using a liquid containing the sample to be separated, while the support means is in the vertical orientation.

3. A method as claimed in claims 1 or 2 wherein the non-electrically conducting liquid is paraffin oil.

4. A method as claimed in claim 1 wherein the first electrophoretic separation medium comprises an IPG strip.

5. A method as claimed in claim 1 wherein the second electrophoretic separation medium comprises a gel slab.

6. A method as claimed in claim 1 wherein the support means comprises a generally planar support.

7. A method as claimed in claim 1 wherein the liquid buffer containing bridging material comprises agarose gel containing a buffer.

* * * * *